US011934970B2

(12) United States Patent
Yamamoto

(10) Patent No.: US 11,934,970 B2
(45) Date of Patent: Mar. 19, 2024

(54) ABDUCTION APPARATUS, ABDUCTION METHOD, AND COMPUTER-READABLE RECORDING MEDIUM

(71) Applicant: NEC Corporation, Tokyo (JP)

(72) Inventor: Kazeto Yamamoto, Tokyo (JP)

(73) Assignee: NEC CORPORATION, Tokyo (JP)

(*) Notice: Subject to any disclaimer, the term of this patent is extended or adjusted under 35 U.S.C. 154(b) by 445 days.

(21) Appl. No.: 17/270,082

(22) PCT Filed: Aug. 27, 2018

(86) PCT No.: PCT/JP2018/031622
§ 371 (c)(1),
(2) Date: Feb. 22, 2021

(87) PCT Pub. No.: WO2020/044413
PCT Pub. Date: Mar. 5, 2020

(65) Prior Publication Data
US 2021/0326735 A1    Oct. 21, 2021

(51) Int. Cl.
G06N 5/04    (2023.01)
G06N 3/092    (2023.01)
(Continued)

(52) U.S. Cl.
CPC ............ G06N 5/041 (2013.01); G06N 3/092 (2023.01); G06F 16/2428 (2019.01); G06F 16/7335 (2019.01); G06N 5/022 (2013.01); G06N 5/025 (2013.01); G06N 7/00 (2013.01); G06N 7/01 (2023.01)

(58) Field of Classification Search
CPC ........ G06N 5/041; G06N 3/092; G06N 5/022; G06N 5/025; G06N 7/00; G06N 7/01; G06F 16/2428; G06F 16/7335
See application file for complete search history.

(56) References Cited

U.S. PATENT DOCUMENTS 9,449,275 B2 * 9/2016 Hubauer ............ G05B 23/0278
11,372,381 B1 * 6/2022 Trowbridge ............ G06N 7/01
(Continued)

FOREIGN PATENT DOCUMENTS

JP    H08-137695 A    5/1996

OTHER PUBLICATIONS

Inoue et Gordon, "A Scalable Weighted Max-SAT Implementation of Propositional Etcetera Abduction" May 2017, AAAI, pp. 1-6. (Year: 2017).*

(Continued)

Primary Examiner — Vincent Gonzales
Assistant Examiner — Chase P. Hinckley

(57) ABSTRACT

An abduction apparatus 1 includes: a probability calculation unit 2 configured to, with respect to each of candidate hypotheses generated using observation information and knowledge information, calculate a probability that the candidate hypothesis holds true as an explanation of the observation information; and a reward selection unit 3 configured to, when the candidate hypothesis holds true, select a reward value regarding the candidate hypothesis that has held true by referring to reward definition information in which a condition that the candidate hypothesis holds true is associated with the reward value.

9 Claims, 10 Drawing Sheets

(51) Int. Cl.
  *G06F 16/242* (2019.01)
  *G06F 16/732* (2019.01)
  *G06N 5/022* (2023.01)
  *G06N 5/025* (2023.01)
  *G06N 7/00* (2023.01)
  *G06N 7/01* (2023.01)

(56) References Cited

U.S. PATENT DOCUMENTS

| | | | |
|---|---|---|---|
| 2017/0024659 A1* | 1/2017 | Stromsten | G06F 16/24578 |
| 2017/0323568 A1* | 11/2017 | Inoue | G08G 1/163 |
| 2018/0260700 A1* | 9/2018 | Nagaraja | G06N 3/044 |
| 2019/0034785 A1* | 1/2019 | Murray | G06N 3/084 |
| 2019/0147353 A1* | 5/2019 | Beller | G06F 16/24534 |
| | | | 706/12 |
| 2019/0348178 A1* | 11/2019 | Eleftherou | G16H 50/50 |
| 2020/0027032 A1* | 1/2020 | Morimura | G06N 7/08 |
| 2021/0279614 A1* | 9/2021 | Kimura | G06N 5/041 |

OTHER PUBLICATIONS

Haarnoja et al., "Latent Space Policies for Hierarchical Reinforcement Learning" Apr. 9, 2018, arXiv: 1804.02808v1, pp. 1-10. (Year: 2018).*

Innes et al., "Reasoning about Unforeseen Possibilities During Policy Learning" Jan. 10, 2018, arXiv: 1801.03331v1, pp. 1-47. (Year: 2018).*

Yamamato et al., "Hierarchical Reinforcement Learning with Abductive Planning" Jun. 28, 2018, arXiv: 1806.10792v1, pp. 1-7. (Year: 2018).*

Dai et al., "Tunneling Neural Perception and Logic Reasoning through Abductive Learning" Feb. 6, 2018, arXiv: 1802.01173v2, pp. 1-27. (Year: 2018).*

Schuller, Peter, "Modeling Variations of First-Order Horn Abduction in Answer Set Programming" Jan. 31, 2018, arXiv: 1512.08899v4, pp. 1-40. (Year: 2018).*

Ignatiev et al., "Propositional Abduction with Implicit Hitting Sets" Apr. 27, 2016, arXiv: 1604.08229v1, pp. 1-20. (Year: 2016).*

Dhamdhere et al., "Abductive Matching in Question Answering" Sep. 10, 2017, arXiv: 1709.03036v1, pp. 1-9. (Year: 2017).*

Kapoor, Sanyam, "Multi-Agent Reinforcement Learning: A Report on Challenges and Approaches" Jul. 25, 2018, arXiv: 1807.09427v1, pp. 1-24. (Year: 2018).*

Yao et al., "Interactive Semantic Parsing for If-Then Recipes via Hierarchical Reinforcement Learning" Aug. 21, 2018, arXiv: 1808.06740v1, pp. 1-13. (Year: 2018).*

Pukancova, Julia, "Direct Approach to ABox Abduction in Description Logics" Apr. 2018, pp. i-129. (Year: 2018).*

Juba et al., "Learning Abduction under Partial Observability" Nov. 25, 2017, arXiv: 1711.04438v3, pp. 1-7. (Year: 2017).*

Zhang et al., "An Improved Algorithm for Learning to Perform Exception-Tolerant Abduction" Feb. 12, 2017, pp. 1257-1265. (Year: 2017).*

International Search Report for PCT Application No. PCT/JP2018/031622, dated Nov. 27, 2018.

Naoya Inoue and Kentaro Inui, "ILP-based Reasoning for Weighted Abduction", In Proceedings of AAAI Workshop on Plan, Activity and Intent Recognition, pp. 25-32, Aug. 2011.

Sato, Taisuke, "Statistical Abduction", Journal of Japanese Society for Artificial Intelligence, May 1, 2010, vol. 25, No. 3, pp. 400-407.*

Yamamoto, Kazeto et al. "Efficient Estimation of Plausible Abductive Hypotheses Using A* Search", IPSJ SIG Technical Report, vol. 2014—NL-217 No. 10, Jun. 26, 2014, pp. 1-9.

English translation of Written opinion for PCT Application No. PCT/JP2018/031622, dated Nov. 27, 2018.

Japanese Office Action for JP Application No. 2020-539187 dated Mar. 1, 2022 with English Translation.

* cited by examiner

Fig.5

QUERY LOGICAL FORMULA: D1

```
food(f)
```

BACKGROUND KNOWLEDGE: D2

```
baked_potato(x) ⇒ food(x): 0.0
potato(x) ⇒ food(x): 0.0
potato(x) ∧ coal(y) ⇒ baked_potato(z): 0.0
potato(P): 0.0
coal(C): 0.5
```

REWARD DEFINITION INFORMATION: D5

```
200 if H ∪ B ⇒ potato(x)
600 if H ∪ B ⇒ baked_potato(x)
```

| NODE ID | LOGICAL FORMULA |
|---------|-----------------|
| 0 | food(f) |
| 1 | potato(f) |
| 2 | potato(P) |
| 3 | f = P |

72

| RULE ID | INFERENCE RULE |
|---------|----------------|
| 0 | baked_potato(x) ⇒ food(x) : 0.0 |
| 1 | potato(x) ⇒ food(x) : 0.0 |
| 2 | potato(x) ∧ coal(y) ⇒ baked_potato(z) : 0.0 |
| 3 | potato(P) : 0.0 |
| 4 | coal(C) : 0.5 |

73

| RULE ID | START POINT NODE ID | END POINT NODE ID |
|---------|---------------------|-------------------|
| 1 | 0 | 1 |
| 3 | 2 | 3 |

74

| UNIFIED NODE ID | NODE ID | NODE ID |
|-----------------|---------|---------|
| 3 | 1 | 2 |

| NODE ID | LOGICAL FORMULA |
|---------|-----------------|
| 0 | food(f) |
| 1 | baked_potato(f) |
| 2 | potato(u1) |
| 3 | coal(u2) |
| 4 | potato(P) |
| 5 | coal(C) |
| 6 | u1 = P |
| 7 | u2 = C |

82

| RULE ID | START POINT NODE ID | END POINT NODE ID |
|---------|---------------------|-------------------|
| 0 | 0 | 1 |
| 2 | 1 | 2, 3 |
| 3 | 4 | – |
| 4 | 5 | – |

83

| UNIFIED NODE ID | NODE ID | NODE ID |
|-----------------|---------|---------|
| 6 | 2 | 4 |
| 7 | 3 | 5 |

ABDUCTION APPARATUS, ABDUCTION METHOD, AND COMPUTER-READABLE RECORDING MEDIUM

This application is a National Stage Entry of PCT/JP2018/031622 filed on Aug. 27, 2018, the contents of all of which are incorporated herein by reference, in their entirety.

TECHNICAL FIELD

The present invention relates to an abduction apparatus and an abduction method for executing abduction, and further relates to a computer-readable recording medium that includes a program for realizing the same recorded thereon.

BACKGROUND ART

According to known abduction processing, first, a set of candidate hypotheses is generated using a query logical formula and background knowledge. The query logical formula is a conjunction of first-order predicate logic literals. Also, the first-order predicate logic literal is an atomic formula in a first-order predicate logic, or a negation of the atomic formula. The background knowledge is a set of inference rules. The inference rules are implication logical formulae.

Next, in such abduction processing, each candidate hypothesis of the generated set is evaluated. Then, a most appropriate candidate hypothesis (solution hypothesis) is selected, from the set of candidate hypotheses, as an explanation regarding the query logical formula based on the evaluations regarding the candidate hypotheses.

Here, when a classification is made based on the definition of an evaluation value, the abduction is roughly categorized into two types, namely Weighted Abduction and probabilistic abduction.

A parameter (cost) for indicating the "importance of explaining this logical formula" is given to a query logical formula in Weighted Abduction. Also, a parameter (weight) for indicating "the reliability that the antecedent holds true, if the consequent holds true" is given to each inference rule included in the background knowledge. Then, when a candidate hypothesis is evaluated, the evaluation value is calculated according to these parameters.

In the probabilistic abduction, each inference rule included in the background knowledge is given a parameter for indicating "the degree of probability that the inference rule holds true". When a candidate hypothesis is evaluated, the probability that inference rules used in the candidate hypothesis hold true at the same time is calculated as the evaluation value.

Note that, as a related technique, Weighted Abduction processing is disclosed in Non-Patent Document 1. According to the disclosed Weighted Abduction processing, a most appropriate candidate hypothesis is selected as the explanation regarding a query logical formula by applying an integer linear planning method.

LIST OF RELATED ART DOCUMENTS

Non-Patent Document

Non-Patent Document 1: Naoya Inoue and Kentaro Inui, "ILP-based Reasoning for Weighted Abduction", Proceedings of AAAI Workshop on Plan, Activity and Intent Recognition, pp. 25-32, August 2011.

SUMMARY

Technical Problems

However, in the abduction as described above, a framework of abduction does not exist in which, when a candidate hypothesis is evaluated, both of the probabilistic evaluation and the evaluation other than the probabilistic evaluation can be performed. Therefore, in Weighted Abduction, when a candidate hypothesis is evaluated, the probabilistic evaluation cannot be performed.

In contrast, in the probabilistic abduction, the importance cannot be changed for each query logical formula, which can be done in Weighted Abduction.

An example object of the present invention is to provide an abduction apparatus and an abduction method in which, when a candidate hypothesis is evaluated, an evaluation other than a probabilistic evaluation can be performed along with the probabilistic evaluation, and a computer-readable recording medium.

Solution to the Problems

To achieve the above-stated example object, an abduction apparatus according to an example aspect of the present invention includes:

a probability calculation unit configured to, with respect to each of candidate hypotheses generated using observation information and knowledge information, calculate a probability that the candidate hypothesis holds true as an explanation of the observation information; and a reward selection unit configured to, when the candidate hypothesis holds true, select a reward value regarding the candidate hypothesis that has held true by referring to reward definition information in which a condition that the candidate hypothesis holds true is associated with the reward value.

Also, to achieve the above-stated example object, an abduction method according to an example aspect of the present invention includes:

calculating, with respect to each of candidate hypotheses generated using observation information and knowledge information, a probability that the candidate hypothesis holds true as an explanation of the observation information; and selecting, when the candidate hypothesis holds true, a reward value regarding the candidate hypothesis that has held true by referring to reward definition information in which a condition that the candidate hypothesis holds true is associated with the reward value.

Furthermore, to achieve the above-stated example object, a computer-readable recording medium according to an example aspect of the present invention is a computer-readable recording medium that includes a program recorded thereon, the program causing a computer to carry out:

calculating, with respect to each of candidate hypotheses generated using observation information and knowledge information, a probability that the candidate hypothesis holds true as an explanation of the observation information; and selecting, when the candidate hypothesis holds true, a reward value regarding the candidate hypothesis that has held true by referring to reward definition information in which a condition that the candidate hypothesis holds true is associated with the reward value.

Advantageous Effects of the Invention

As described above, according to the present invention, when a candidate hypothesis is evaluated, an evaluation other than probabilistic evaluation can be performed along with the probabilistic evaluation.

BRIEF DESCRIPTION OF THE DRAWINGS

FIG. 5 is a diagram illustrating an example of a query logical formula, a background knowledge, and a reward definition information.

FIG. 7 is a diagram illustrating an example of a data structure of the candidate hypothesis.

FIG. 8 is a diagram illustrating an example of the data structure of the candidate hypothesis.

EXAMPLE EMBODIMENT

Example Embodiment

Hereinafter, an example embodiment of the present invention will be described with reference to FIGS. 1 to 9.

[Apparatus Configuration]

Figure 1:
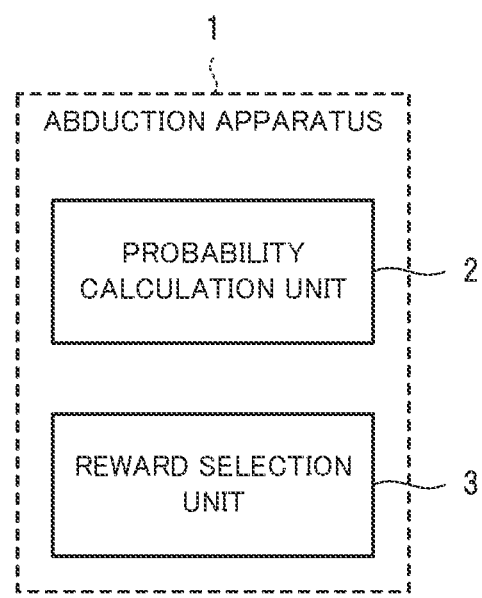
FIG. 1 is a diagram illustrating an example of an abduction apparatus.

First, the configuration of an abduction apparatus 1 according to the present example embodiment will be described using FIG. 1. FIG. 1 is a diagram illustrating an example of the abduction apparatus.

The abduction apparatus 1 shown in FIG. 1 is an apparatus that can perform, when a candidate hypothesis is evaluated, an evaluation other than a probabilistic evaluation along with the probabilistic evaluation. Also, as shown in FIG. 1, the abduction apparatus 1 includes a probability calculation unit 2 and a reward selection unit 3.

Among these units, the probability calculation unit 2 calculates, with respect to each candidate hypothesis generated using observation information (query logical formula) and knowledge information (background knowledge), a probability that the candidate hypothesis holds true as the explanation of the query logical formula. The reward selection unit 3, when a candidate hypothesis holds true, selects a reward value regarding the candidate hypothesis that has held true, by referring to reward definition information in which the condition that the candidate hypothesis holds true is associated with a reward value.

In this way, in the present example embodiment, the probability that a candidate hypothesis holds true and a reward value when the candidate hypothesis holds true can be calculated, and therefore an evaluation other than a probabilistic evaluation can be performed along with the probabilistic evaluation.

[System Configuration]

Figure 2:
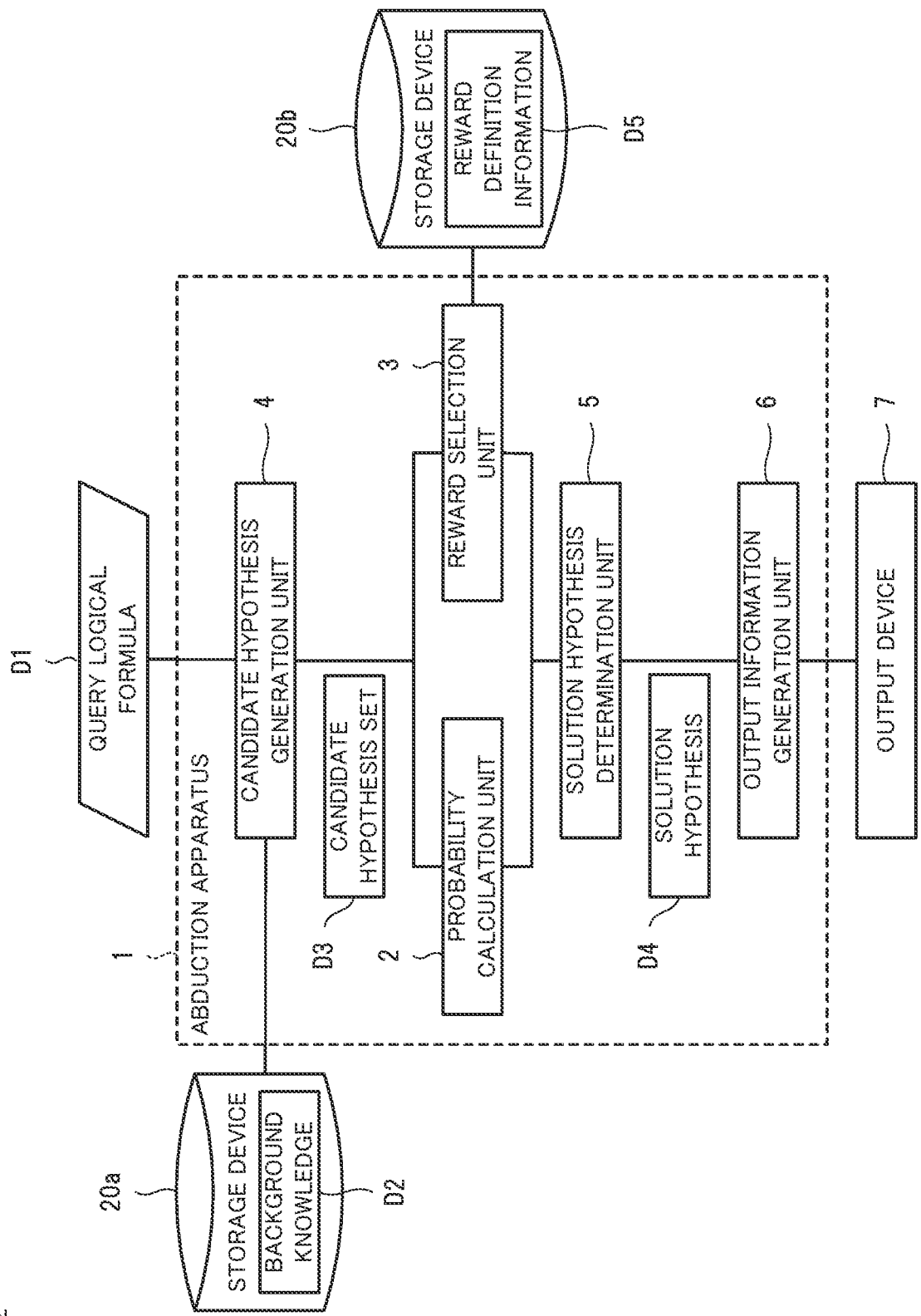
FIG. 2 is a diagram illustrating an example of a system including the abduction apparatus.

Next, the configuration of the abduction apparatus 1 according to the present example embodiment will be more specifically described using FIG. 2. FIG. 2 is a diagram illustrating an example of a system including the abduction apparatus.

As shown in FIG. 2, the abduction apparatus 1 according to the present example embodiment includes a candidate hypothesis generation unit 4, a solution hypothesis determination unit 5, an output information generation unit 6, and an output device 7, in addition to the probability calculation unit 2 and the reward selection unit 3. Also, the system including the abduction apparatus 1 includes storage devices 20a and 20b. The storage devices 20a and 20b may be provided inside of the abduction apparatus 1, or may be provided outside thereof. Note that the storage devices 20a and 20b may be the same storage device, or may be different storage devices.

Figure 3:
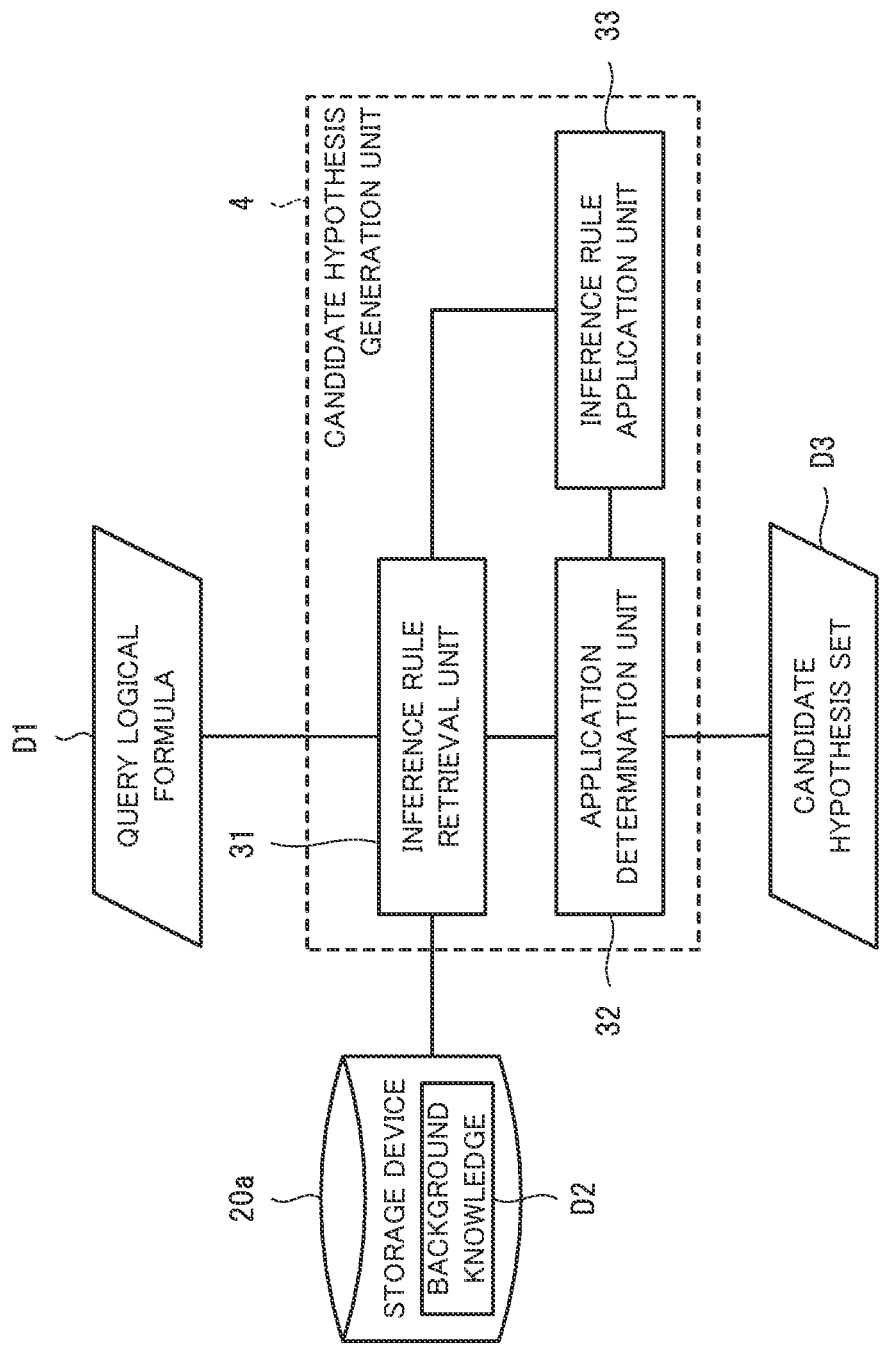
FIG. 3 is a diagram illustrating an example of a candidate hypothesis generation unit.

The candidate hypothesis generation unit 4 acquires a query logical formula D1 and a background knowledge D2 stored in the storage device 20a, and generates a candidate hypothesis set D3 including a plurality of candidate hypotheses using processing for generating candidate hypotheses. Also, the candidate hypothesis generation unit 4 includes an inference rule retrieval unit 31, an application determination unit 32, and an inference rule application unit 33, as shown in FIG. 3. FIG. 3 is a diagram illustrating an example of the candidate hypothesis generation unit.

The query logical formula D1 is a conjunction of first-order predicate logic literals. The first-order predicate logic literal is an atomic formula or a negation thereof in the first-order predicate logic.

The background knowledge D2 is a set of inference rules. The inference rule is an implication logical formula, and is expressed by a logical formula in a form shown in formula (1).

[Math. 1]

$$P_1 \wedge P_2 \wedge \ldots \wedge P_N \Rightarrow Q_1 \wedge Q_2 \wedge \ldots \wedge Q_M \quad (1)$$

$P_i$, $Q_j$: first-order predicate logic literal

Note that it is assumed that the variables included in the antecedents in the inference rules are all universally quantified, and the variables included in only the consequents of the inference rules are all existentially quantified. Hereinafter, even in a case where the quantifier is omitted, each variable is quantified based on the assumption described above.

Also, it is assumed that a case where the antecedent is empty, that is, N=0 in formula (1) is allowed, and such a rule is called a fact, which indicates that the consequent unconditionally holds true. In the following, the antecedent and implication symbol will be omitted regarding a fact, and the face is simply expressed by a logical formula in a form of formula (2).

[Math. 2]

$$Q_1 \wedge Q_2 \wedge \ldots \wedge Q_M \quad (2)$$

Also, a parameter needed for probability calculation in the probability calculation unit 2 is given to each of the inference rules. What type of parameter is given is determined based on the model that is adopted by the probability calculation unit 2. For example, when the Etcetera Abduction is used, each inference rule is given a negative logarithmic value of the probability that the inference rule holds true. Refer to formula (3).

[Math. 3]

$$-\log\{p(\wedge_{i=1}^{M} Q_i | \wedge_{j=1}^{N} P_j)\} \quad (3)$$

The candidate hypothesis set D3 is a set of candidate hypotheses that is output from the candidate hypothesis generation unit 4. The candidate hypothesis is a directed non-cycling hypergraph in which first-order predicate logic literals are nodes, and an edge that connects hypernodes expresses a relationship "which literal is explained by which literal using which inference rule". The terminal node that is reached by tracing back edges matches one of the first-order predicate logic literals included in the query logical formula. Also, the first-order predicate logic literal corresponding to an unexplained node, that is, a node that is not included in any end points of edges is called an element hypothesis logical formula.

The inference rule retrieval unit 31 performs processing in which an inference rule is retrieved that can be applied backwardly with respect to the current candidate hypothesis set D3. Specifically, the inference rule retrieval unit 31 retrieves an inference rule in which a manner of variable substitution is present so as to be equivalent with the conjunction of the first-order predicate logic literals included in the candidate hypothesis, with respect to the first-order predicate logic literals included in the consequent of the inference rule. For example, with respect to a candidate hypothesis q(A), an inference rule p(x)⇒q(x) is backwardly applicable, and an inference rule p(x)⇒r(x) is not backwardly applicable.

The application determination unit 32 performs end determination of processing for generating a candidate hypothesis. Specifically, if an inference rule that can be newly applied to the current candidate hypothesis set is not present, the application determination unit 32 ends the processing of the candidate hypothesis generation unit, and outputs the candidate hypotheses that have been generated until this point in time.

The inference rule application unit 33 performs processing for generating a new candidate hypothesis by applying the inference rule retrieved by the inference rule retrieval unit 31 to the candidate hypothesis set D3. Specifically, the inference rule application unit 33 generates a new candidate hypothesis q(A)∧p (A) by applying the inference rule p(x)⇒q(x) to the candidate hypothesis q(A).

Note that the candidate hypothesis generation unit 4 may generate the candidate hypothesis set D3 using the processing shown in FIG. 3, or may also generate the candidate hypothesis set D3 using another method.

The probability calculation unit 2 acquires candidate hypotheses from the candidate hypothesis set D3 generated by the candidate hypothesis generation unit 4, and calculates, with respect to each of the candidate hypotheses, a probability that the candidate hypothesis holds true as an explanation of the query logical formula D1, as an output. Specifically, the probability calculation unit 2 uses probabilistic abduction models such as Probabilistic Cost-based Abduction, Etcetera Abduction, and MLNs (Markov Logic Networks)-formulated Abduction.

For example, when the Probabilistic Cost-based Abduction is used, the probability of a candidate hypothesis is calculated as a total sum of costs assigned to the respective inference rules used in the candidate hypothesis. Therefore, in the Probabilistic Cost-based Abduction, the probability $P_H$ regarding the candidate hypothesis is defined as shown in formula (4).

[Math. 4]

$$P_H = e^{-w} \quad (4)$$

w: total sum of parameters given to inference rules

Also, when a probability based on the Etcetera Abduction is calculated, the probability P H regarding the candidate hypothesis is defined as shown in formula (5).

[Math. 5]

$$P_H = \Pi_{r \in B(H)} e^{-w_r} \quad (5)$$

H: candidate hypothesis
r: inference rule
B(H): set of inference rules used in candidate hypothesis
$w_r$: parameter in Etcetera Abduction assigned to inference rule r The reward selection unit 3 acquires candidate hypotheses of the candidate hypothesis set D3 and reward definition information D5 stored in the storage device 20b as inputs, and outputs reward values that are obtained when the respective candidate hypotheses hold true. The reward definition information D5 is a set of pairs of a reward value and its payment condition (reward definition), and may be freely defined by a user according to the task.

Specifically, the reward selection unit 3, when a candidate hypothesis holds true, selects a reward value regarding the candidate hypothesis that has held true, by referring to the reward definition information D5 in which the condition that the candidate hypothesis holds true is associated with a reward value. For example, the reward selection unit 3, with respect to each of the candidate hypotheses, enumerates items in the reward definition information D5 in which the payment condition is satisfied, calculates a total sum of these reward values, and outputs the reward values of the candidate hypothesis.

The solution hypothesis determination unit 5 determines, from candidate hypotheses, a candidate hypothesis (solution hypothesis D4) that is a best explanation regarding the candidate hypotheses using the evaluation value calculated based on the probability and the reward value. Specifically, the solution hypothesis determination unit 5 determines a candidate hypothesis, from the candidate hypothesis set D3, regarding which the evaluation value obtained by multiplying the probability and the reward value is largest.

More specifically, the solution hypothesis is obtained by formulating the problem as some combinatorial optimization problem such as an integer linear planning problem or a weighted satisfiability problem, and retrieving the optimum solution using a corresponding solver. In such a case, the evaluation value obtained by multiplying the probability and the reward value is expressed as a combinatorial optimization problem, and therefore in many cases, the problem is formulated as a combinatorial optimization problem in which the total sum of logarithmic values of the probability and the reward value is maximized.

Note that, when a plurality of pieces of reward definition information are present, with respect to all considerable combinations of rewards, the terms of a target function are separately defined. For example, when a condition of paying a reward R1 and a condition of paying a reward R2 are defined as the reward definition information D5, the terms regarding the reward in a target function of the combinatorial optimization problem need to be defined regarding four cases, namely a case where the reward value is 0, a case where the reward value is R1, a case where the reward value is R2, and a case where the reward value is R1+R2.

Also, a reward (default reward) that is given on a condition that none of the conditions of other rewards is satisfied can be defined, as the reward definition. In this way, "what degree of groundless hypothesis can be allowed as the solution hypothesis" can be controlled by the amount of default reward. Specifically, a hypothesis candidate regarding which a value obtained by multiplying the probability and the reward value is less than the default reward will not be selected as the solution hypothesis, and therefore, as a result of increasing the default reward, only the useful candidate hypotheses, that is, candidate hypotheses that are expected to obtain a high reward with a high probability can be output.

The output information generation unit 6 acquires at least the probability, the reward value, and the solution hypothesis, generates output information to be output to the output device 7, based on at least one of the probability, the reward value, and the solution hypothesis or by combining two or more of these items, and transmits the generated output information to the output device 7. Note that the output information generation unit 6 may generate the output information for outputting the candidate hypothesis set D3 to the output device 7 along with any one of, or two or more of the probability, the reward value, and the solution hypothesis.

The output device 7 receives output information that has been converted to an outputtable format from the output information generation unit 6, and outputs an image, a sound, and the like that are generated based on the output information. The output device 7 includes an image display device using liquid crystal, organic EL (Electro Luminescence), or a CRT (Cathode Ray Tube), and furthermore, a sound output device such as a speaker, for example. Note that the output device 7 may also be a printing device such as a printer.

[Apparatus Operations]

Figure 4:
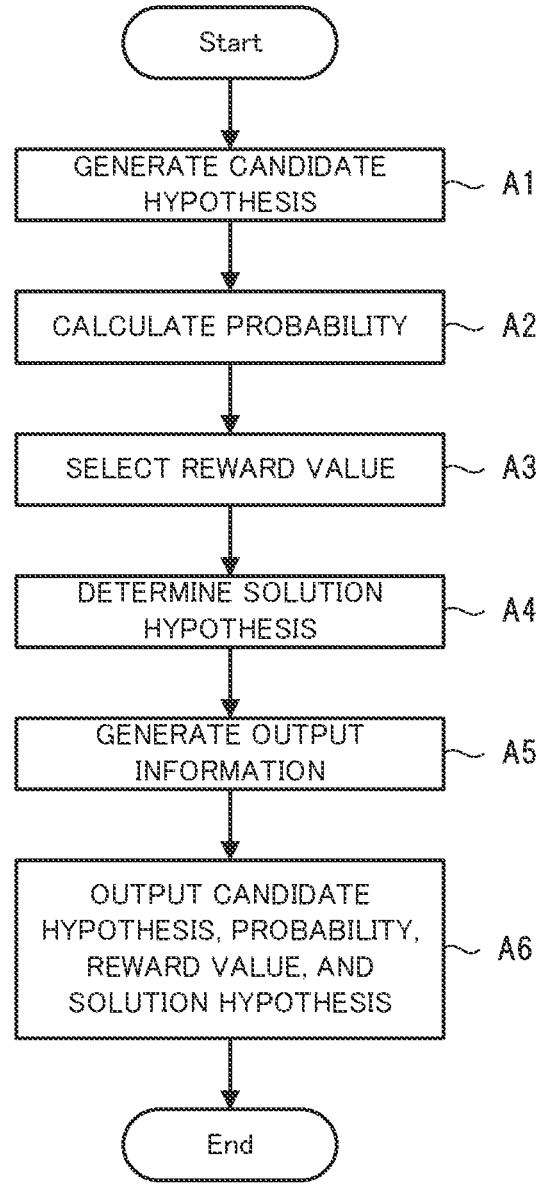
FIG. 4 is a diagram illustrating an example of operations of the abduction apparatus.
Figure 6A:
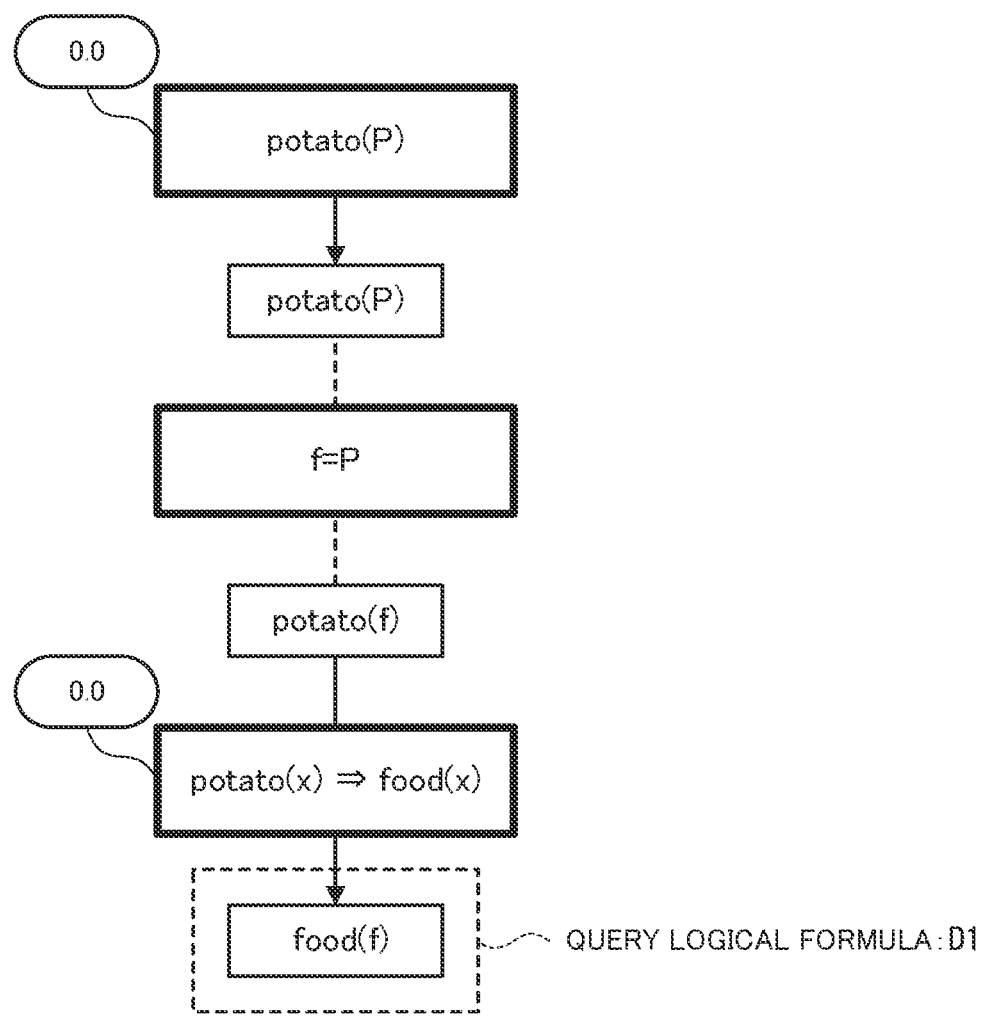
FIG. 6A is a diagram illustrating an example of a candidate hypothesis.
Figure 6B:
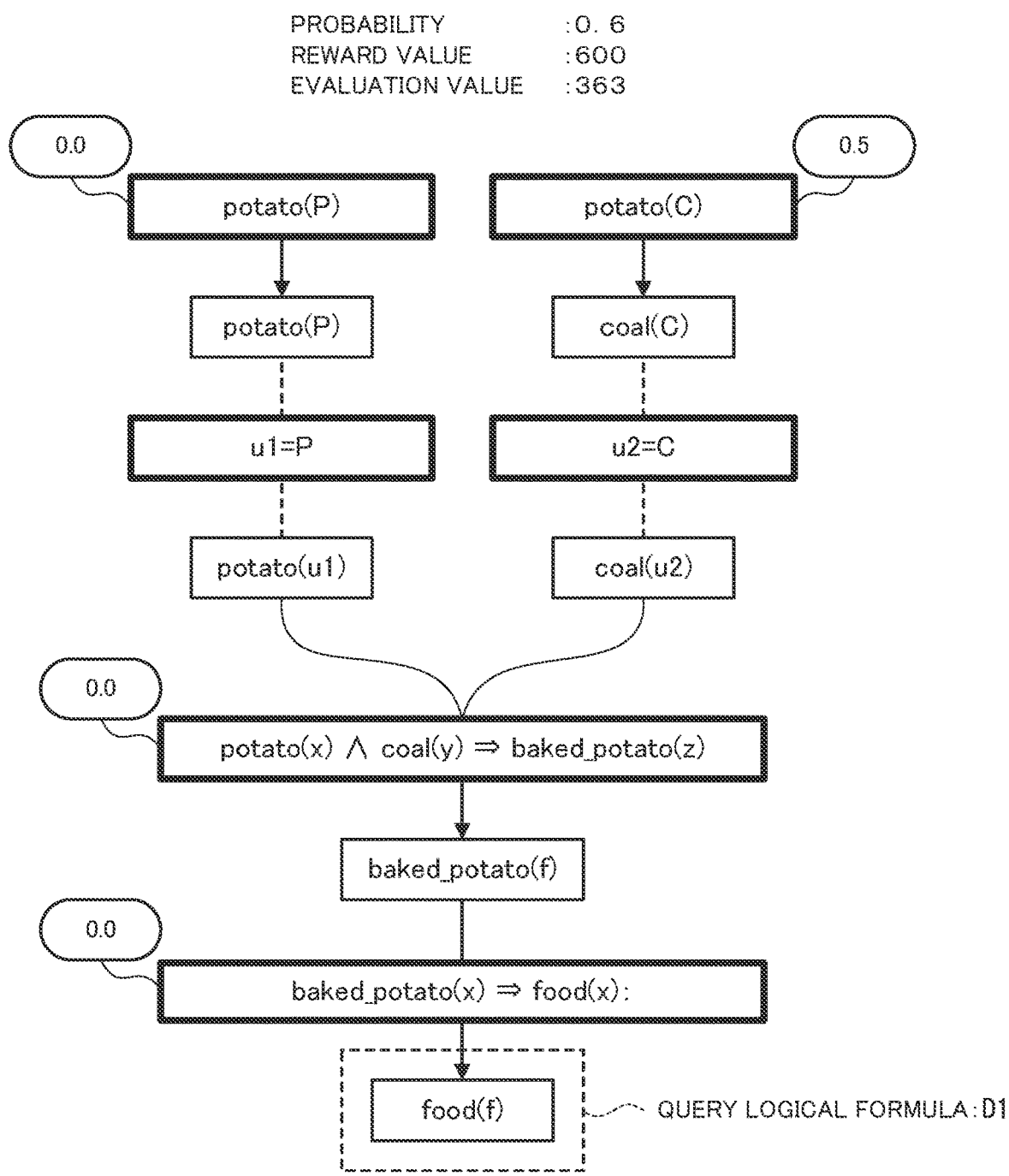
FIG. 6B is a diagram illustrating an example of the candidate hypothesis.

Next, the operations of the abduction apparatus 1 according to the example embodiment of the present invention will be described using FIGS. 4, 5, 6A, 6B, 7 and 8. FIG. 4 is a diagram illustrating an example of operations of the abduction apparatus. FIG. 5 is a diagram illustrating an example of the query logical formula, the background knowledge, and the reward definition information. FIGS. 6A and 6B are diagrams illustrating an example of the candidate hypothesis. FIGS. 7 and 8 are diagrams illustrating an example of the data structure of the candidate hypothesis. In the following description, FIGS. 2 to 8 will be referred to as appropriate. Furthermore, in the present example embodiment, the abduction method is carried out by causing the abduction apparatus 1 to operate. Therefore, the following description of the operations of the abduction apparatus 1 applies to the abduction method according to the present example embodiment.

As shown in FIG. 4, first, the candidate hypothesis generation unit 4 acquires the query logical formula D1 and the background knowledge D2, and generates a candidate hypothesis set D3 including a plurality of candidate hypotheses (step A1).

Next, the probability calculation unit 2 acquires candidate hypotheses from the candidate hypothesis set D3, and calculates a probability that each of the candidate hypotheses hold true as the explanation of the query logical formula D1, as an output (step A2). The reward selection unit 3 acquires candidate hypotheses of the candidate hypothesis set D3 and the reward definition information D5, and outputs reward values that are obtained when the respective candidate hypotheses hold true (step A3). Note that the order of processing in steps A2 and A3 may be reversed, or may be executed at the same time.

Next, the solution hypothesis determination unit 5 determines the solution hypothesis D4 from the candidate hypotheses using the evaluation values calculated based on the probabilities and the reward values (step A4).

Next, the output information generation unit 6 acquires at least the probability, the reward value, and the solution hypothesis, and generates output information to be output to the output device 7 (step A5). The output device 7 receives the output information that has been converted to an outputtable format from the output information generation unit 6, and outputs an image, a sound, and the like that are generated based on the output information (step A6).

Next, the operations of the abduction apparatus 1 will be more specifically described. For example, a planning task in which materials are collected and food is created will be described.

The query logical formula D1 is assumed to be a conjunction that logically expresses a target state that "some food will be finally obtained". Refer to query logical formula D1 shown in FIG. 5.

The background knowledge D2 gives inference rules that logically expresses pieces of knowledge that are "if x is a baked potato, then x is food", "if x is a potato, then x is food", "if x is a potato and y is coal, then a baked potato can be made", "already having a potato", and "it is possible to obtain coal". Refer to the background knowledge D2 shown in FIG. 5.

The reward definition information D5 is defined such that when the finally obtained food is a baked potato, a reward value "600" is given, and when the finally obtained food is a potato, a reward "200" is given. Refer to the reward definition information D5 shown in FIG. 5.

In step A1, the candidate hypothesis generation unit 4 acquires the query logical formula D1 and the background knowledge D2, and generates the candidate hypothesis set D3. Note that the initial state of the candidate hypothesis set D3 is assumed to include only a candidate hypothesis including only the query logical formula D1, that is, "food (f)".

Specifically, in step A1, first, the inference rule retrieval unit 31 of the candidate hypothesis generation unit 4 retrieves, from the background knowledge D2, an inference rule that can be backwardly applied to the candidate hypothesis set D3. For example, with respect to an inference rule "potato(x)⇒food(x)", as a result of substituting "x=f", the consequent of the inference rule matches a portion of the candidate hypothesis, and therefore this inference rule is selected as being applicable backwardly.

Next, in step A1, the inference rule selected by the inference rule retrieval unit 31 is applied to the candidate hypothesis set backwardly, in the inference rule application unit 33 of the candidate hypothesis generation unit 4. For example, if the inference rule "potato(x)⇒food(x)" is applied to the initial state of the candidate hypothesis set D3 described above, a new candidate hypothesis "potato(f)∧food(f)" is added to the candidate hypothesis set D3.

Also, in the general abduction, if a pair of first-order predicate logic literals are present, in the facts in the candidate hypotheses generated by backward inference and the background knowledge, that become the same when a variable that is existentially quantified is substituted by a different variable, the candidate hypothesis when such a variable substitution is performed is separately generated.

For example, if an inference rule "f=P" is assumed with respect to the above-mentioned candidate hypothesis "potato(f)∧food(f)", the first-order predicate logic literal "potato (f)" in the candidate hypothesis becomes the same formula as the fact (inference rule) "potato(P)" in the background knowledge. With this, the candidate hypothesis "potato(f)∧food(f)∧f=P" obtained when such a variable substitution is performed is also added to the candidate hypothesis set. Such a procedure is called as unification operation.

In the Etcetera Abduction, a constraint is present that all of the element hypotheses in the respective candidate hypotheses must be unified with facts, and therefore two candidate hypotheses as shown in FIGS. 6A and 6B are output as the candidate hypothesis set D3 in this example.

Next, in step A2, the probability calculation unit 2 calculates the probabilities of the respective candidate hypotheses with the candidate hypothesis set D3 being the input. Specifically, when the Etcetera Abduction is used as a model for calculating the probability that the hypothesis holds true, as the probability calculation unit 2, the parameters (e.g., actual value and the like) given to the inference rules included in the background knowledge D2 correspond to negative logarithmic values of the probabilities that the rule hold true.

For example, the probability that an inference rule to which "0.0" is assigned as the parameter of the inference rule holds true is "1.0". Also, the probability that an inference rule to which "0.5" is assigned as the parameter of the inference rule holds true is "0.6". Refer to formulas (6) and (7).

[Math. 6]

$$P_H = e^{-0.0} = 1.0 \quad (6)$$

[Math. 7]

$$P_H = e^{-0.0} \cong 0.6 \quad (7)$$

Also, the probability regarding the candidate hypothesis shown in FIG. 6B is as shown in formula (8), for example.

[Math. 8]

$$P_H = (e^{-0.5} \cdot e^{-0.0} \cdot e^{-0.0} \cdot e^{-0.0} \cdot e^{-0.0}) = e^{-0.5} \quad (8)$$

Next, in step A3, the reward selection unit 3 receives the candidate hypothesis set D3 and the reward definition information D5, and outputs reward values of the respective candidate hypotheses. For example, the candidate hypothesis shown in FIG. 6A satisfies only the condition of the first row in the reward definition information D5 in FIG. 5, and therefore the reward value is "200". Also, the candidate hypothesis shown in FIG. 6B satisfies only the condition of the second row in the reward definition information D5 in FIG. 5, and therefore the reward value is "600".

Next, in step A4, the solution hypothesis determination unit 5 determines a solution hypothesis D4 that is the best explanation from the candidate hypothesis set D3 using the evaluation values calculated based on probabilities and reward values. Specifically, the solution hypothesis determination unit 5 outputs a candidate hypothesis regarding which the evaluation value obtained by multiplying its probability and reward value is largest, from the candidate hypothesis set D3. For example, regarding the two candidate hypotheses shown in FIGS. 6A and 6B, the evaluation value regarding the candidate hypothesis in FIG. 6A is "200*1.0=200", and the evaluation value regarding the candidate hypothesis in FIG. 6B is "600*0.6=363", and therefore the candidate hypothesis in FIG. 6B is determined as the solution hypothesis D4.

Also, a method is proposed in Non-Patent Document 1 in which the procedure for selecting the best hypothesis is expressed as an equivalent integer linear planning problem, and this problem is solved using an external integer linear planning problem solver, and as a result, the best hypothesis is derived at a high speed. In the present invention as well, the best hypothesis may be retrieved by a similar method.

Next, in step A5, the output information generation unit 6 acquires at least the probability, the reward value, and the solution hypothesis, generates output information to be output to the output device 7 using any one of the probability, the reward value, and the solution hypothesis or by combining two or more of the items, and transmits the generated output information to the output device 7. Note that the output information generation unit 6 may generate output information for outputting the candidate hypothesis set D3 to the output device 7 along with any one of or two or more of the probability, the reward value, and the solution hypothesis. For example, as shown in FIGS. 6A and 6B, it is conceivable to display the candidate hypothesis, the probability, the reward value, and the solution hypothesis.

Note that the output information generation unit 6 generates information for a display as shown in FIGS. 6A and 6B using pieces of information 71 to 74 and 81 to 83 shown in FIGS. 7 and 8, for example. The information 71 shown in FIG. 7 is information in which "node IDs" for identifying logical formulas included in the candidate hypothesis shown in FIG. 6A are associated with logical formulas. The information 72 is information in which "rule IDs" for identifying inference rules included in the candidate hypothesis that are used in FIGS. 6A and 6B are associated with inference rules.

The information 73 is information in which edges (solid line arrows shown in FIG. 6A), shown in FIG. 6A, that are included in the candidate hypothesis are associated with "start node IDs" indicating the start points, "end point node IDs" indicating the end points, and "rule IDs". The information 74 is information in which a unified edge (broken line shown in FIG. 6A), shown in FIG. 6A, that is included in the candidate hypothesis is associated with a unified node pair "node IDs" and a "unified node ID" generated by unification.

The information 81 shown in FIG. 8 is information in which "node IDs" for identifying logical formulas, shown in FIG. 6B, that are included in the candidate hypothesis are associated with logical formulas. The information 82 is information in which edges (solid line arrows shown in FIG. 6B), shown in FIG. 6B, that are included in the candidate hypothesis are associated with "start node IDs" indicating the start points, "end point node IDs" indicating the end points, and "rule IDs". The information 83 is information in which unified edges (broken line shown in FIG. 6B), shown in FIG. 6B, that are included in the candidate hypothesis are associated with unified node pairs "node IDs" and "unified nodes ID" generated by unification.

Next, in step A6, the output device 7 receives the output information that has been converted to an outputtable format from the output information generation unit 6, and outputs an image, a sound, and the like that are generated based on the output information.

Effects According to Present Example Embodiment

As described above, according to the present example embodiment, as a result of utilizing the new framework of abduction described above, the probability that a candidate hypothesis holds true and a reward value obtained when the candidate hypothesis holds true can be calculated, and therefore evaluation other than a probabilistic evaluation can be performed along with the probabilistic evaluation. That is, according to the present example embodiment, a flexible reward definition and evaluation based on the probability theory can be performed at the same time, which cannot be realized with a known method, and therefore the method can be applied to tasks in a wider range than that of the known method in a practical use as well.

Also, with respect to the obtained solution hypothesis, the probability that the solution hypothesis holds true and the reward obtained when the solution hypothesis holds true can be separately presented, and therefore information that is more useful than the known method can be provided to the user.

Also, the probability that a candidate hypothesis holds true is calculated, and a value obtained by multiplying the probability and a reward value is used as the evaluation value, and therefore a candidate hypothesis regarding which the expected value of an reward value obtained based on suitably defined reward definition information is largest can be derived.

Also, the probability and the reward value are separately calculated until the evaluation value is calculated, and therefore, the probability and the reward value can be output separately for each of the candidate hypotheses.

Also, regarding the design of the reward selection unit 3, the reward value can be defined with respect to a case where the candidate hypothesis satisfies a specific structure condition in addition to the case where the candidate hypothesis was able to explain the query logical formula, and therefore modeling of a task in which a matter (query logical formula) desired to be explained in a planning task or the like is different from the matter regarding the reward value can also be performed. For example, supporting of an expert having expert knowledge to perform various tasks can be automated.

Moreover, compared with a case where similar inference is performed using a known probabilistic abduction model, the best hypothesis can be efficiently obtained. The reason is that, in the case where the known probabilistic abduction is used, with respect to all of the combinations of individual reward definitions, the probabilities that the respective combinations of rewards holds true need to be obtained by inference, but in the present example embodiment, as a result of using the new framework of abduction described above, the best hypothesis can be obtained even in one time of inference.

[Program]

A program according to the present example embodiment need only be a program for causing a computer to perform steps A1 to A6 shown in FIG. 4. The abduction apparatus and the abduction method according to the present example embodiment can be realized by installing this program on a computer and executing the program. In this case, a processor of the computer functions as the candidate hypothesis generation unit 4, the probability calculation unit 2, the reward selection unit 3, the solution hypothesis determination unit 5, and the output information generation unit 6, and performs processing.

Also, the program according to the present example embodiment may also be executed by a computer system that includes a plurality of computers. In this case, for example, each of the computers may function as any of the candidate hypothesis generation unit 4, the probability calculation unit 2, the reward selection unit 3, the solution hypothesis determination unit 5, and the output information generation unit 6.

[Physical Configuration]

Figure 9:
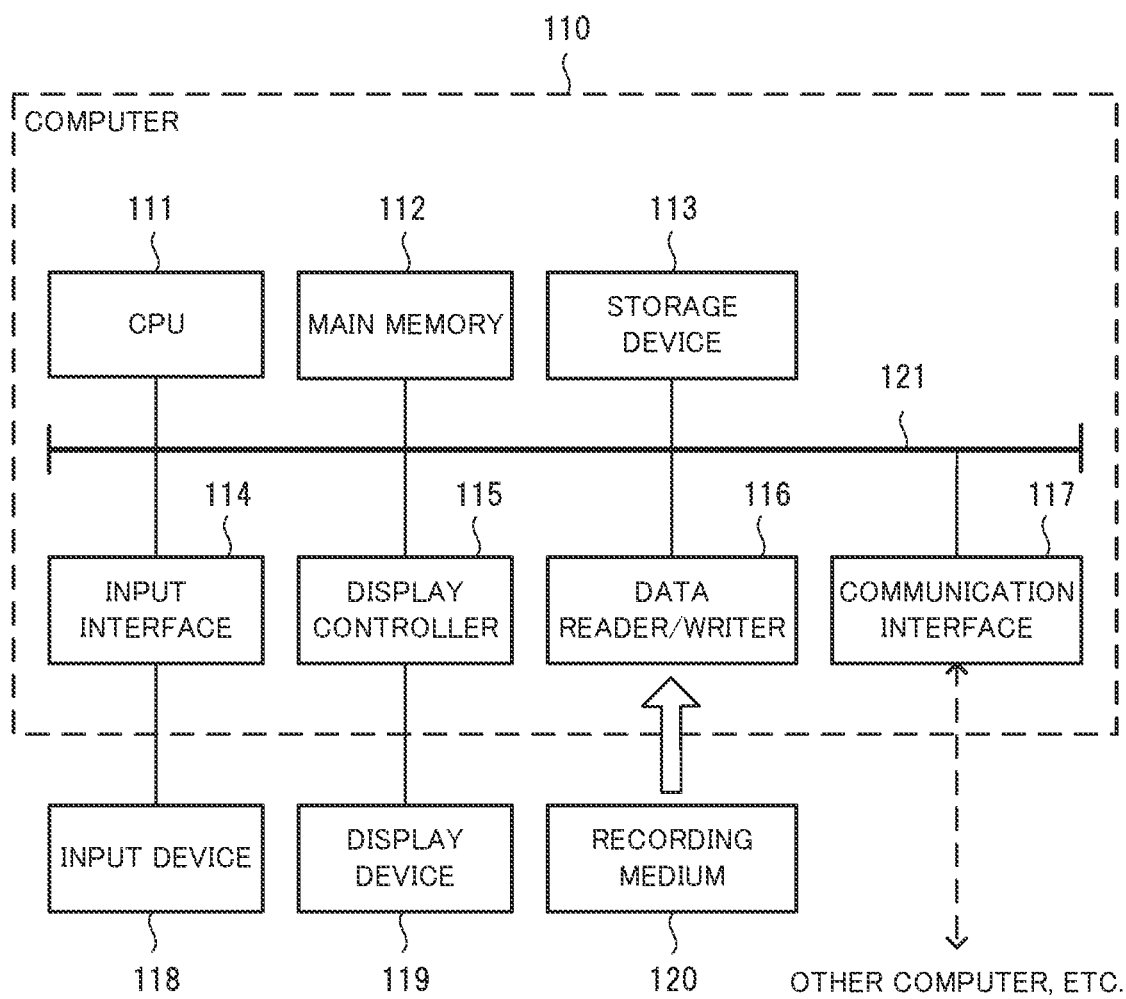
FIG. 9 is a diagram illustrating an example of a computer that realizes the abduction apparatus.

A description will now be given, with reference to FIG. 9, of a computer that realizes the abduction apparatus by executing the program according to the present example embodiment. FIG. 9 is a block diagram illustrating an example of a computer that realizes the abduction apparatus according to the present example embodiment of the present invention.

As shown in FIG. 9, a computer 110 includes a CPU 111, a main memory 112, a storage device 113, an input interface 114, a display controller 115, a data reader/writer 116, and a communication interface 117. These units are connected to each other via a bus 121 so as to be able to communicate data. Note that the computer 110 may also include, in addition to the CPU 111 or in place of the CPU 111, a GPU (Graphics Processing Unit), or an FPGA (Field-Programmable Gate Array).

The CPU 111 loads the program (codes) according to the present example embodiment that is stored in the storage device 113 to the main memory 112 and executes the program in a predetermined order, thereby performing various kinds of computation. The main memory 112 is typically a volatile storage device such as a DRAM (Dynamic Random Access Memory). The program according to the present example embodiment is provided in a state of being stored in a computer-readable recording medium 120. Note that the program according to the present example embodiment may also be distributed on the Internet to which the computer is connected via the communication interface 117.

Specific examples of the storage device 113 may include a hard disk drive, a semiconductor storage device such as a flash memory, and the like. The input interface 114 mediates data transmission between the CPU 111 and input devices 118 such as a keyboard and a mouse. The display controller 115 is connected to a display device 119 and controls a display in the display device 119.

The data reader/writer 116 mediates data transmission between the CPU 111 and the recording medium 120, reads out the program from the recording medium 120, and writes, in the recording medium 120, the results of processing performed by the computer 110. The communication interface 117 mediates data transmission between the CPU 111 and other computers.

Specific examples of the recording medium 120 may include a general-purpose semiconductor storage device such as a CF (Compact Flash (registered trademark)) or an SD (Secure Digital), a magnetic recording medium such as a Flexible Disk, and an optical recording medium such as a CD-ROM (Compact Disk Read Only Memory).

Note that the abduction apparatus 1 according to the present example embodiment may also be realized using hardware that corresponds to each of the units, rather than a computer in which the program is installed. Furthermore, the abduction apparatus 1 may be partially realized by a program, and the remainder may be realized by hardware.

[Supplementary Note]

With respect to the example embodiment described above, furthermore the following supplementary notes are disclosed. Part of, or the entire present example embodiment described above can be expressed by the following (Supplementary note 1) to (Supplementary note 12), but is not limited thereto.

(Supplementary Note 1)

A abduction apparatus including:

a probability calculation unit configured to, with respect to each of candidate hypotheses generated using observation information and knowledge information, calculate a probability that the candidate hypothesis holds true as an explanation of the observation information; and a reward selection unit configured to, when the candidate hypothesis holds true, select a reward value regarding the candidate hypothesis that has held true by referring to reward definition information in which a condition that the candidate hypothesis holds true is associated with the reward value.

(Supplementary Note 2)

The abduction apparatus according to supplementary note 1, further including:

a solution hypothesis determination unit configured to determine a solution hypothesis that is a best explanation regarding the candidate hypothesis from the candidate hypotheses, using an evaluation value that is calculated based on the probability and the reward value.

(Supplementary Note 3)

The abduction apparatus according to supplementary note 2, wherein the solution hypothesis determination unit calculates the evaluation value by multiplying the probability and the reward value, and determines the candidate hypothesis regarding which the evaluation value is largest as the solution hypothesis.

(Supplementary Note 4)

The abduction apparatus according to supplementary note 2 or 3, further including: an output information generation unit configured to generate output information to be output to an output device from any one of the probability, the reward value, and the solution hypothesis, or by combining two or more of these items.

(Supplementary Note 5)

A abduction method, including:

(a) a step of calculating, with respect to each of candidate hypotheses generated using observation information and knowledge information, a probability that the candidate hypothesis holds true as an explanation of the observation information; and (b) a step of selecting, when the candidate hypothesis holds true, a reward value regarding the candidate hypothesis that has held true by referring to reward definition information in which a condition that the candidate hypothesis holds true is associated with the reward value.

(Supplementary Note 6)

The abduction method according to supplementary note 5, further including:

(c) a step of determining a solution hypothesis that is a best explanation regarding the candidate hypothesis from the candidate hypotheses, using an evaluation value that is calculated based on the probability and the reward value.

(Supplementary Note 7)

The abduction method according to supplementary note 6, wherein, in the (c) step, the evaluation value is calculated by multiplying the probability and the reward value, and the candidate hypothesis regarding which the evaluation value is largest is determined as the solution hypothesis.

(Supplementary Note 8)

The abduction method according to supplementary note 6 or 7, further including:

(d) a step of generating output information to be output to an output device from any one of the probability, the reward value, and the solution hypothesis, or by combining two or more of these items.

(Supplementary Note 9)

A computer-readable recording medium that includes a program recorded thereon, the program causing a computer to carry out:

(a) a step of calculating, with respect to each of candidate hypotheses generated using observation information and knowledge information, a probability that the candidate hypothesis holds true as an explanation of the observation information; and (b) a step of selecting, when the candidate hypothesis holds true, a reward value regarding the candidate hypothesis that has held true by referring to reward definition information in which a condition that the candidate hypothesis holds true is associated with the reward value.

(Supplementary Note 10)

The computer readable recording medium that includes the program according to supplementary note 9 recorded thereon, the program further causing the computer to carry out:

(c) a step of determining a solution hypothesis that is a best explanation regarding the candidate hypothesis from the candidate hypotheses, using an evaluation value that is calculated based on the probability and the reward value.

(Supplementary Note 11)

The computer readable recording medium that includes the program according to supplementary note 10 recorded thereon, wherein, in the (c) step, the evaluation value is calculated by multiplying the probability and the reward value, and the candidate hypothesis regarding which the evaluation value is largest is determined as the solution hypothesis.

(Supplementary Note 12)

The computer readable recording medium that includes the program according to supplementary note 10 or 11 recorded thereon, the program further causing the computer to carry out:

(d) a step of generating output information to be output to an output device from any one of the probability, the reward value, and the solution hypothesis, or by combining two or more of these items.

The present invention of the present application has been described above with reference to the present example embodiment, but the present invention of the present application is not limited to the above present example embodiment. The configurations and the details of the present invention of the present application may be changed in various manners that can be understood by a person skilled in the art within the scope of the invention of the present application.

INDUSTRIAL APPLICABILITY

As described above, according to the present invention, when a candidate hypothesis is evaluated, an evaluation other than probabilistic evaluation can be performed along with the probabilistic evaluation. The present invention is useful in a field in which explanation generation, situation understanding, or the like using a query logical formula and background knowledge is needed. Specifically, the present invention can be applied to a medical system, and an automatic system for performing legal advice, risk detection, or the like.

REFERENCE SIGNS LIST

1 Abduction apparatus
2 Probability calculation unit
3 Reward selection unit
4 Candidate hypothesis generation unit
5 Solution hypothesis determination unit
6 Output information generation unit
7 Output device
20a, 20b Storage device
31 Inference rule retrieval unit
32 Application determination unit
33 Inference rule application unit
D1 Query logical formula
D2 Background knowledge
D3 Candidate hypothesis set
D4 Solution hypothesis
D5 Reward definition information
110 Computer
111 CPU
112 Main memory
113 Storage device
114 Input interface
115 Display controller
116 Data reader/writer
117 Communication interface
118 Input devices
119 Display device
120 Recording medium
121 Bus

What is claimed is:

1. An abduction apparatus comprising:
at least one memory storing instructions; and
at least one processor configured to access the at least one memory and execute the instructions to:
calculate, with respect to each of a plurality of candidate hypotheses that are generated using observation information and knowledge information and that are each a directed non-cycling hypergraph in which first order predicate logic literals are nodes connected by edges that each express a relationship as to which literal is explained by which other literal using which inference rule, a probability that the candidate hypothesis holds true as an explanation of the observation information;
select, based on the probability calculated for each candidate hypothesis, one or more of the candidate hypotheses that hold true as the explanation;
select, for each of the one or more of the candidate hypotheses that have been selected, a reward value by referring to reward definition information in which a condition that the each of the one or more of the candidate hypotheses is associated with the reward value; and
generate output information to be output to an output device from any one of the probability of each of the one or more candidate hypotheses that have been selected, the reward value of each of the one or more candidate hypotheses that have been selected, the one or more candidate hypotheses that have been selected, and a combination of any of the probability of the probability of each of the one or more candidate hypotheses that have been selected, the reward value of each of the one or more candidate hypotheses that have been selected, the one or more candidate hypotheses that have been selected.

2. The abduction apparatus according to claim 1, wherein the at least one processor is configured to access the at least one memory and execute the instructions to further:
determine, from the one or more of the candidate hypotheses that have been selected, a solution hypothesis that is a best explanation of the observation information, using an evaluation value that is calculated for each of the one or more of the candidate hypotheses that have been selected based on the probability and the reward value.

3. The abduction apparatus according to claim 2, wherein the evaluation value is calculated by multiplying the probability and the reward value, and the candidate hypothesis of the one or more of the candidate hypotheses that have been selected for which the evaluation value is largest.

4. An abduction method, comprising:
calculating, by a processor and with respect to each of a plurality of candidate hypotheses that are generated using observation information and knowledge information and that are each a directed non-cycling hypergraph in which first order predicate logic literals are nodes connected by edges that each express a relationship as to which literal is explained by which other literal using which inference rule, a probability that the candidate hypothesis holds true as an explanation of the observation information;
selecting, by processor and based on the probability calculated for each candidate hypothesis, one or more of the candidate hypotheses that hold true as the explanation;
selecting, by the processor and for each of the one or more of the candidate hypotheses that have been selected, a reward value by referring to reward definition information in which a condition that the each of the one or more of the candidate hypotheses is associated with the reward value; and
generating, by the processor, output information to be output to an output device from any one of the probability of each of the one or more candidate hypotheses that have been selected, the reward value of each of the one or more candidate hypotheses that have been selected, the one or more candidate hypotheses that have been selected, and a combination of any of the probability of the probability of each of the one or more candidate hypotheses that have been selected, the reward value of each of the one or more candidate hypotheses that have been selected, the one or more candidate hypotheses that have been selected.

5. The abduction method according to claim 4, further comprising:
determining, by the processor and from the one or more of the candidate hypotheses that have been selected, a solution hypothesis that is a best explanation of the observation information, using an evaluation value that is calculated for each of the one or more of the candidate hypotheses that have been selected based on the probability and the reward value.

6. The abduction method according to claim 5, wherein the evaluation value is calculated by multiplying the probability and the reward value, and the candidate hypothesis of the one or more of the candidate hypotheses that have been selected for which the evaluation value is largest.

7. A non-transitory computer-readable recording medium storing a program that when executed by a computer causes the computer to carry out:
- calculating, with respect to each of a plurality of candidate hypotheses that are generated using observation information and knowledge information and that are each a directed non-cycling hypergraph in which first order predicate logic literals are nodes connected by edges that each express a relationship as to which literal is explained by which other literal using which inference rule, a probability that the candidate hypothesis holds true as an explanation of the observation information;
- selecting, based on the probability calculated for each candidate hypothesis, one or more of the candidate hypotheses that hold true as the explanation;
- selecting, by the processor and for each of the one or more of the candidate hypotheses that have been selected, a reward value by referring to reward definition information in which a condition that the each of the one or more of the candidate hypotheses is associated with the reward value; and
- generating, output information to be output to an output device from any one of the probability of each of the one or more candidate hypotheses that have been selected, the reward value of each of the one or more candidate hypotheses that have been selected, the one or more candidate hypotheses that have been selected, and a combination of any of the probability of the probability of each of the one or more candidate hypotheses that have been selected, the reward value of each of the one or more candidate hypotheses that have been selected, the one or more candidate hypotheses that have been selected.

8. The non-transitory computer readable recording medium according to claim 7, wherein when executed by the computer the instructions cause the computer to further carry out:
- determining, from the one or more of the candidate hypotheses that have been selected, a solution hypothesis that is a best explanation of the observation information, using an evaluation value that is calculated for each of the one or more of the candidate hypotheses that have been selected based on the probability and the reward value.

9. The non-transitory computer readable recording medium according to claim 8,
wherein evaluation value is calculated by multiplying the probability and the reward value, and the candidate hypothesis of the one or more of the candidate hypotheses that have been selected for which the evaluation value is largest.

* * * * *